(12) United States Patent
Shim et al.

(10) Patent No.: US 10,428,096 B2
(45) Date of Patent: Oct. 1, 2019

(54) POLYKETONE POLYMERIZATION CATALYST

(71) Applicants: HYOSUNG CHEMICAL CORPORATION, Seoul (KR); ST PHARM CO., LTD., Siheung-si, Gyeonggi-do (KR)

(72) Inventors: Jae Yoon Shim, Gunpo-si (KR); Sun Kue Kim, Ansan-si (KR); Hae Souk Cho, Anyang-si (KR); Ji Hwan Choi, Incheon (KR); Geun Jho Lim, Seoul (KR); Sun Ki Chang, Gunpo-si (KR); Min Kyu Kim, Ansan-si (KR); In Hyeok Baek, Ansan-si (KR)

(73) Assignees: HYOSUNG CHEMICAL CORPORATION, Seoul (KR); ST PHARM CO., LTD., Siheung-si, Gyeonggi-do (KR)

( * ) Notice: Subject to any disclaimer, the term of this patent is extended or adjusted under 35 U.S.C. 154(b) by 174 days.

(21) Appl. No.: 14/906,233

(22) PCT Filed: Jul. 16, 2014

(86) PCT No.: PCT/KR2014/006451
§ 371 (c)(1),
(2) Date: Jan. 19, 2016

(87) PCT Pub. No.: WO2015/009061
PCT Pub. Date: Jan. 22, 2015

(65) Prior Publication Data
US 2016/0333036 A1 Nov. 17, 2016

(30) Foreign Application Priority Data

Jul. 17, 2013 (KR) .................. 10-2013-0084203

(51) Int. Cl.
| | | |
|---|---|---|
| *C07F 9/00* | (2006.01) | |
| *C07F 9/655* | (2006.01) | |
| *C07F 9/50* | (2006.01) | |
| *C08G 67/02* | (2006.01) | |

(52) U.S. Cl.
CPC .......... *C07F 9/6552* (2013.01); *C07F 9/5027* (2013.01); *C08G 67/02* (2013.01)

(58) Field of Classification Search
None
See application file for complete search history.

(56) References Cited

FOREIGN PATENT DOCUMENTS

| | | | |
|---|---|---|---|
| JP | S 64-20230 | | 1/1989 |
| JP | S 64-60629 | | 3/1989 |
| KR | 10-2006-0057719 A | | 5/2006 |
| KR | 10-2006-0060787 A | | 6/2006 |
| KR | 10-2008-0061174 A | | 7/2008 |
| WO | WO 01/02463 A1 | | 1/2001 |
| WO | WO 200102463 | * | 1/2001 ............ C08G 67/02 |

OTHER PUBLICATIONS

International Search Report dated Oct. 17, 2014 issued in Application No. PCT/KR2014/006451.
Tiddo J. Mooibroek et al.: "NMR Spectroscopic Studies of Palladium (II) Complexes of Bidentate Diphenyphosphate Ligands with Acetate and Tosylate Anions: Complex Formation and Structures", European Journal of Inorganic Chemistry—Chemische Berichte, vol. 2010, No. 2, Jan. 1, 2010 (Jan. 1, 2010), pp. 298-310, XP55325485, DE ISN: 1434-1948, DOI: 10.1002/ejic.200900974 *table 1*.
Japanese Office Action dated Mar. 1, 2017 issued in Application No. 2016-527932.
European Search Report dated Mar. 8, 2017 issued in Application No. 14826323.9.

* cited by examiner

*Primary Examiner* — Yun Qian
(74) *Attorney, Agent, or Firm* — Revolution IP, PLLC

(57) ABSTRACT

Provided are a novel polyketone polymerization catalyst and a method of preparing a ligand, which can reduce production costs and can enable commercial mass synthesis by using ((2,2-dimethyl-1,3-dioxane-5,5-diyl)bis(methylene))bis(bis(2-methoxyphenyl)phosphine) as a ligand constituting the polykeytone polymerization catalyst, the ligand having a simple structure and a small molecular weight while having high activity.

6 Claims, No Drawings

POLYKETONE POLYMERIZATION CATALYST

CROSS-REFERENCE TO RELATED PATENT APPLICATIONS

This application is a U.S. National Stage Application under 35 U.S.C. § 371 of PCT Application No. PCT/KR2014/006451, filed Jul. 16, 2014, which claims priority to Korean Patent Application No. 10-2013-0084203, filed Jul. 17, 2013, whose entire disclosures are hereby incorporated by reference.

TECHNICAL FIELD

The present invention relate to polyketone polymerization catalysts, and more specifically, to a novel polyketone polymerization catalyst, and a method of preparing a ligand, the polyketone polymerization catalyst and the method being capable of reducing production costs and enabling commercial mass synthesis by using ((2,2-dimethyl-1,3-dioxane-5,5-diyl)bis(methylene))bis(bis(2-methoxyphenyl)phosphine) as a ligand constituting the polyketone polymerization catalyst, the ligand having a simple structure and a small molecular weight while having high activity.

BACKGROUND ART

A copolymer of carbon monoxide and an ethylenically unsaturated compound, especially, polyketone having a structure in which repeat units derived from carbon monoxide and repeat units derived from the ethylenically unsaturated compound are substantially alternately connected to each other, is a material that can be applied in various uses because the polyketone has an excellent mechanical property and thermal property, and high wear resistance, chemical resistance, and gas barrier property.

Since a high-molecular compound of alternating copolymer polyketone has a high mechanical property, a high thermal property, and excellent economics, it is deemed to be useful as an engineering plastic material. For example, since the polyketone has high wear resistance, it is useful for use in parts such as a gear of a vehicle; since the polyketone has high chemical resistance, it is useful for use in lining materials of chemical transport pipes and the like; and since the polyketone has a high gas barrier property, it is useful for use in lightweight gasoline tanks and the like.

In addition, in the case where polyketone having a ultra-high molecular weight and an intrinsic viscosity of 2 or more is used in a fiber, high stretching can be realized, and the fiber can have high strength and elastic modulus as a fiber oriented in a stretching direction. Thus, it becomes a very suitable material to be used as stiffeners for belts, rubber hoses, and the like, stiffeners for tire cords and concrete, building materials, and materials for industry.

A polymerization catalyst used in preparing the polyketone is typically composed of the system of Pd(II)/bidentate phosphine ligand/acid.

For example, a palladium (II) acetate/1,3-bis[di(2-methoxyphenyl)phosphino]propane/trifluoroaceticacid(Pd(OAc)2-BDOMPP-TFA) system was developed and was commercialized by Shell Company in 1999.

1,3-bis[di(2-methoxyphenyl)phosphino]propane
(F.wt: 532.54 g/mol)

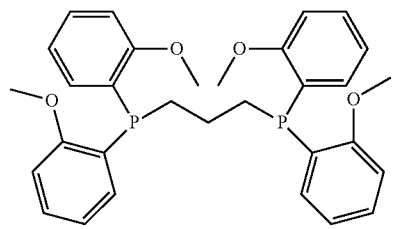

The development of a high activity polymerization catalyst used in preparing polyketone has been performed based on the modification of a bisphosphine ligand among three components of the catalyst.

Typically, 2,2-dimethoxy-1,3-bis[di(2-methoxyphenyl)phosphino]propane, 3,3-bis-[bis-(2-methoxyphenyl)phosphanylmethyl]-1,5-dioxa-spiro[5,5]undecane, and the like that are beyond the activity of BDOMPP have been known. Although they averagely express polymerization activity more than two times than the BDOMPP system, it is disadvantageous in that they are not easy to be commercially synthesized, and have high prices.

In addition, a synthesis method described in the patent (WO2001-002463A1) regarding 3,3-bis-[bis-(2-methoxyphenyl)phosphanylmethyl]-1,5-dioxa-spiro[5,5]undecane is a dangerous reaction that can be caused only in a Lab scale in which lithium is used, and is problematic in that it is inappropriate for the method to commercially perform mass production.

2,2-dimethoxy-1,3-bis[di(2-methoxyphenyl)phosphino]propane (F.wt: 560.59 g/mol)

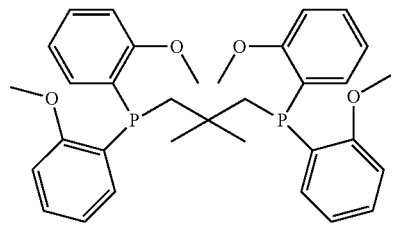

3,3-bis-[bis-(2-methoxyphenyl)phosphanylmethyl]-1,5-dioxa-spiro[5,5]undecane (WO2001-002463A1)
(F.wt: 672.73 g/mol)

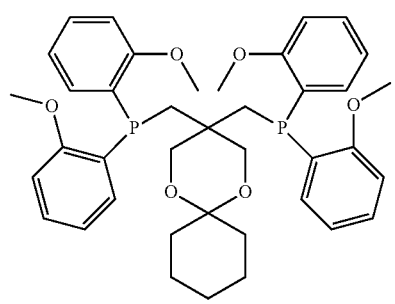

Accordingly, the development for novel polyketone polymerization catalysts that can be economically easily and commercially synthesized in large quantities while expressing high polymerization activity, and synthesis processes have been needed.

PRIOR ART DOCUMENT

Patent Document (Patent Document 1) International Laid-Open Publication No. WO 2001-002463

DISCLOSURE OF INVENTION

Technical Problem

The present invention has been devised for solving the above problems, and an object of the present invention is to provide a polyketone polymerization catalyst including a specific ligand having a simple structure and a small molecular weight while exhibiting high activity, and a method (synthesis process) of commercially preparing the ligand in large quantities with low preparation costs.

Solution to Problem

In order to solve the problems, according to an aspect of the present invention, there is provided a polyketone polymerization catalyst, including: (A) a metal ion; (B) ((2,2-dimethyl-1,3-dioxane-5,5-diyl)bis(methylene))bis(bis(2-methoxyphenyl)phosphine) represented by following Formula 1 as a ligand; and (C) an acid.

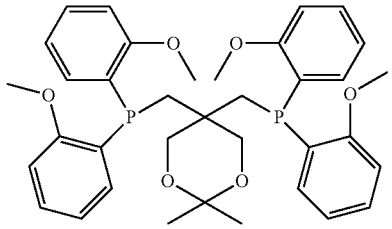

In addition, the metal ion of (A) may be a transition metal ion belonging to Group VIII.

Further, the acid of (C) may be a trifluoroacetic acid), a trifluoromethanesulfonic acid, a p-toluenesulfonic acid, a sulfuric acid, or a maleic acid.

Moreover, a molar ratio of component (A) and component (B) to component (C) may be 1:7 to 1:20.

Also, according to another aspect of the present invention, there is provided a method of preparing a ligand for use in a polyketone polymerization catalyst, the method including: obtaining ((2,2-dimethyl-1,3-dioxane-5,5-diyl)bis(methylene))bis(bis(2-methoxyphenyl)phosphine) using bis(2-methoxyphenyl)phosphine, 5,5-bis(bromomethyl)-2,2-dimethyl-1,3-dioxane, and sodium hydride (NaH).

Furthermore, the method of preparing a ligand for use in a polyketone polymerization catalyst may further include: (a) putting bis(2-methoxyphenyl)phosphine and dimethyl sulfoxide (DMSO) in a reaction vessel under a nitrogen atmosphere, and adding sodium hydride at room temperature and stirring the mixture; (b) adding 5,5-bis(bromomethyl)-2,2-dimethyl-1,3-dioxane and dimethyl sulfoxide to the obtained mixture, and then performing stirring to react it; (c) injecting methanol after completing of the reaction and performing stirring; (d) adding toluene and water and washing an oily layer with water after separating the oily layer from the water, and then performing drying with anhydrous sodium sulfate, thereby performing vacuum filtration and decompression concentration; and (e) recrystallizing a residue with methanol to obtain ((2,2-dimethyl-1,3-dioxane-5,5-diyl)bis(methylene))bis(bis(2-methoxyphenyl)phosphine).

Advantageous Effects of Invention

The present invention provides a novel polyketone polymerization catalyst that can express catalyst activity in the highest level while reducing production costs and production prices by introducing ((2,2-dimethyl-1,3-dioxane-5,5-diyl)bis(methylene))bis(bis(2-methoxyphenyl)phosphine) having high activity, a relatively simple structure, and a low molecular weight as a ligand for use in the polyketone polymerization catalyst.

In addition, according to a method of preparing a ligand for use in the polyketone polymerization catalyst of the present invention, ((2,2-dimethyl-1,3-dioxane-5,5-diyl)bis(methylene))bis(bis(2-methoxyphenyl)phosphine) can be commercially synthesized in large quantities using an easy process under a safe environment in which no lithium is used.

BEST MODE FOR CARRYING OUT THE INVENTION

Hereinafter, the present invention will be described.
Polyketone Polymerization Catalyst A polyketone polymerization catalyst according to the present invention includes: (A) a metal ion; (B) ((2,2-dimethyl-1,3-dioxane-5,5-diyl)bis(methylene))bis(bis(2-methoxyphenyl)phosphine) as a ligand; and (C) an acid.

The kind of the metal ion is not specially limited, and a transition metal ion belonging to Group 8, 9, 10 or 11 of the periodic table may be used. For example, the metal ions may be composed of a compound of Ni and Cu, which is easy to get, and cheap, and a palladium compound which is preferable in terms of the yield and molecular weight of polyketone, especially, palladium (II) acetate, which is preferable in terms of catalyst activity and the improvement of intrinsic viscosity. In one preferred embodiment, the metal ion may be a transition metal ion belonging to Group 8 of the periodic table, for example, Fe, Ru, Os, and the like.

Since the suitable value of a usage amount of the metal ion (or a transition metal compound) is changed according to the kind of a selected ethylenically unsaturated compound or other polymerization conditions, the range thereof may not be uniformly limited. However, the amount may range from 0.01 to 100 millimole per liter based on a capacity of a typical reaction band, more specifically, about 0.01-10 millimole. Therein, the capacity of the reaction band refers to liquid capacity of a reactor. In addition, when palladium (II) acetate is used as a transition metal compound constituting a catalyst composition, it is appropriate that the amount thereof ranges from about 0.001 to 0.1 mole.

The polyketone polymerization catalyst according to the present invention results from introducing ((2,2-dimethyl-1,3-dioxane-5,5-diyl)bis(methylene))bis(bis(2-methoxyphenyl)phosphine) represented by following formula 1 as a ligand with regard to a metal ion/ligand/acid system.

[Formula 1]

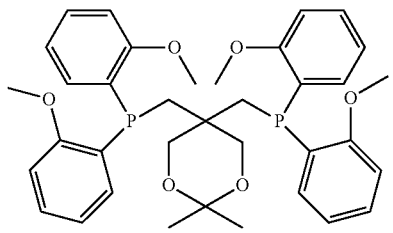

The ((2,2-dimethyl-1,3-dioxane-5,5-diyl)bis(methylene))bis(bis(2-methoxyphenyl)phosphine) has a simpler structure and a low molecular weight while exhibiting an activity expression equivalent to that of 3,3-bis-[bis-(2-methoxyphenyl)phosphanylmethyl]-1,5-dioxa-spiro[5,5]undecane that is known as exhibiting the highest activity among polyketone polymerization catalysts introduced up to date. As a result, the polyketone polymerization catalyst according to the present invention can secure the highest activity in the relevant field, can have reduced preparation costs and cost prices.

Comparison of Molecular Weights (Formula Weights)
((2,2-dimethyl-1,3-dioxane-5,5-diyl)bis(methylene))bis(bis(2-methoxyphenyl) phosphine)→F.wt: 632.66 g/mol
3,3-bis-[bis-(2-methoxyphenyl)phosphanylmethyl]-1,5-dioxa-spiro[5,5]undecane→F.wt: 672.73 g/mol The amount of the ligand contained in the catalyst composition may range from 1 to 1.2 (mole) equivalent compared to the transition metal compound, this range being preferable in view of catalyst activity, intrinsic viscosity, economic catalyst preparation, and the like.

The acid constitutes a negative ion in the catalyst system according to the present invention, and the kind of acids is not specifically limited. For example, as the acid, an organic acid having a pKa of 4 or less, such as a trifluoroacetic acid (or trifluoroacetate), a trifluoromethanesulfonic acid, a p-toluenesulfonic acid, and a maleic acid; an inorganic acid having a pKa of 4 or less, such as a perchloric acid, a sulfuric acid, a nitric acid, a phosphoric acid, a heteropoly acid, tetrafluorobroic acid, a hexafluorophosphoric acid, and a fluorosilicic acid; and a boron compound, such as trispentafluorophenyl borane, trisphenylcarbeniumtetrakis(pentafluorophenyl) borate and the like may be used alone or by mixing at least two materials of them.

As one detailed example, it is preferable to use a trifluoroacetic acid, a trifluoromethanesulfonic acid, a p-toluenesulfonic acid, a sulfuric acid, or a maleic acid in view of the improvement of intrinsic viscosity.

In the catalyst composition, the amount of the acid may range from 6 to 20 (mole) equivalent compared to the transition metal compound, a molar ratio of the metal ion and the ligand to the acid may range from 1:7 to 1:20, the ranges being preferable in view of catalyst activity, intrinsic viscosity, economic catalyst preparation and the like.

The method of preparing the polyketone polymerization catalyst is not specifically limited, and the polyketone polymerization catalyst may be prepared by a typical method in the relevant field using (2,2-dimethyl-1,3-dioxane-5,5-diyl)bis(methylene))bis(bis(2-methoxyphenyl)phosphine) as a ligand.

For example, the catalyst system of the present invention may be configured by adding an acid to a precursor synthesized from the metal ion and the ligand, namely, ((2,2-dimethyl-1,3-dioxane-5,5-diyl)bis(methylene))bis(bis(2-methoxyphenyl)phosphine). In addition, the catalyst system of the present invention may be provided in the form of a catalyst composition including the transition metal compound, ((2,2-dimethyl-1,3-dioxane-5,5-diyl)bis(methylene))bis(bis(2-methoxyphenyl)phosphine), and the negative ion of the acid.

Method of Preparing Ligand for Polyketone Polymerization Catalyst

According to another aspect of the present invention, there is provided a method of preparing a ligand for the polyketone polymerization catalyst, the method being characterized by obtaining ((2,2-dimethyl-1,3-dioxane-5,5-diyl)bis(methylene))bis(bis(2-methoxyphenyl)phosphine) using bis(2-methoxyphenyl)phosphine, 5,5-bis(bromomethyl)-2,2-dimethyl-1,3-dioxane and sodium hydride (NaH).

Unlike a conventional method of synthesizing 3,3-bis-[bis-(2-methoxyphenyl)phosphanylmethyl]-1,5-dioxa-spiro[5,5]undecane, the method of preparing the ligand for the polyketone polymerization catalyst according to the present invention may commercially synthesize ((2,2-dimethyl-1,3-dioxane-5,5-diyl)bis(methylene))bis(bis(2-methoxyphenyl)phosphine) in large quantities using an easy process under a safe circumstance in which no lithium is used.

In one detailed example, the method of preparing the ligand for the polyketone polymerization catalyst according to the present invention may include: (a) putting bis(2-methoxyphenyl)phosphine and dimethyl sulfoxide (DMSO) in a reaction vessel under a nitrogen atmosphere, and adding sodium hydride at room temperature and stirring the mixture; (b) adding 5,5-bis(bromomethyl)-2,2-dimethyl-1,3-dioxane and dimethyl sulfoxide to the obtained mixture and performing stirring to react it: (c) injecting methanol after completing of the reaction and performing stirring; (d) adding toluene and water and washing an oily layer with water after separating the oily layer from the water, and then performing drying with anhydrous sodium sulfate, thereby performing vacuum filtration and decompression concentration; and (e) recrystallizing a residue with methanol to obtain ((2,2-dimethyl-1,3-dioxane-5,5-diyl)bis(methylene))bis(bis(2-methoxyphenyl)phosphine).

Hereinafter, the present invention will be described in greater detail with reference to examples. However, these examples are only intended for convenient understanding of the present invention, and the scope of the present invention should not be limited to these examples in either case.

Example

Synthesis of 5,5-bis(bromomethyl)-2,2-dimethyl-1,3-dioxane 2,2-(bromomethyl)propane-1,3-diol (1 kg, 3.8 mol) was dissolved in 4 L of a dichloromethane under a nitrogen atmosphere.

2,2-dimethoxypropane (596 g, 5.7 mol) was added to the mixture, and cooling was performed out until an inner temperature reached 0 to 5° C.

A concentrated sulfuric acid (7 g, 18.8 mmol) was added with maintenance of the inner temperature, and the resultant mixture was then stirred for 5 hours at an inner temperature of 0~5° C.

The resultant mixture was washed two times with a sodium hydrogen carbonate containing aqueous solution and was washed with water, and was then dried with anhydrous sodium sulfate, thereby obtaining a desired product (1.11 kg, 96.4%) by depressurizing and concentrating the solvent.

NMR(CDCl3): 3.79 (s, 4H), 3.57 (s, 4H), 1.41 (s, 6H)

Synthesis of ((2,2-dimethyl-1,3-dioxane-5,5-diyl)bis(methylene))bis(bis(2-methoxyphenyl)phosphine)

Bis(2-methoxyphenyl)phosphine [see Claudio Bianchini, Eur. J. Inorg. Chem., 2005, 4794-4800] (1 kg, 4.06 mol) and 11 kg of a dimethyl sulfoxide were put in a reaction vessel under a nitrogen atmosphere, sodium hydrogen (60%) (325 g, 8.12 mol) was added to the mixture at room temperature, the resultant mixture was then stirred for 1 hour.

A mixture solution of 5,5-bis(bromomethyl)-2,2-dimethyl-1,3-dioxane (736 g, 2.84 mol) and 5.5 kg of a dimethyl sulfoxide was slowly added, and stirring was then carried out for 2-4 hours.

2 L of a methanol was slowly added after completion of the reaction, and stirring was then carried out.

10 L of a toluene and 10 L of a water were put, an oily layer was washed after separating the oily layer from the water, and drying was then performed with anhydrous sodium sulfate, thereby subjecting the solvent to vacuum filtration and decompression concentration.

A residue was recrystallized with methanol, thereby obtaining ((2,2-dimethyl-1,3-dioxane-5,5-diyl)bis(methylene))bis(bis(2-methoxyphenyl)phosphine).

$^1$H NMR (CDCl3): 7.26~7.16(m, 8H), 6.87~6.75(m, 8H), 3.92(s, 4H), 3.70(s, 12H), 2.51(d, 4H), 1.44(s, 6H)

$^{31}$P NMR(CDCl3): −46.04

((2,2-dimethyl-1,3-dioxane-5,5-diyl)bis(methylene))bis(bis(2-methoxyphenyl)phosphine) (F.wt: 632.66 g/mol)

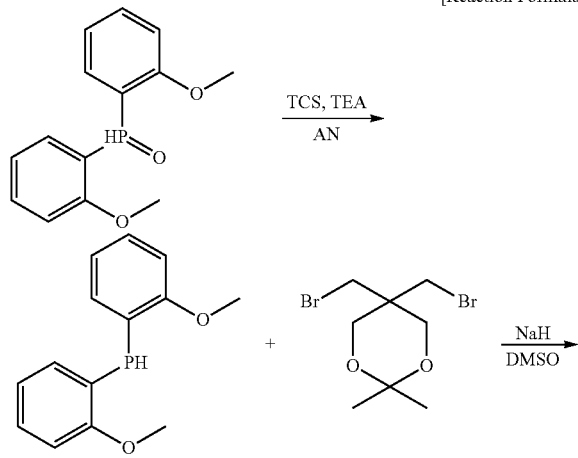

[Reaction Formula]

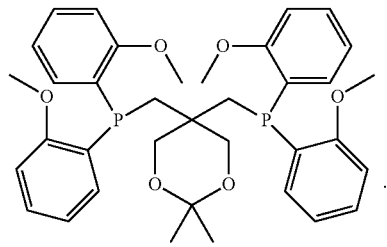

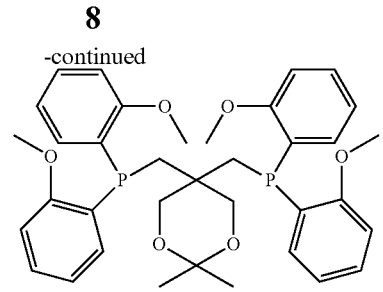

As previously described, in the detailed description of the invention, having described the detailed exemplary embodiments of the invention, it should be apparent that modifications and variations can be made by persons skilled without deviating from the spirit or scope of the invention. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims and their equivalents.

What is claimed is:

1. A polyketone polymerization catalyst, consisting of:
   (A) a metal ion;
   (B) ((2,2-dimethyl-1,3-dioxane-5,5-diyl)bis(methylene))bis(bis(2-methoxyphenyl)phosphine) represented by following Formula 1 as a ligand; and
   (C) an acid, wherein a molar ratio of component (A) and component (B) to component (C) is 1:7 to 1:20

[Formula 1]

2. The polyketone polymerization catalyst of claim 1, wherein the metal ion of (A) is composed of a compound of Ni and Cu.

3. The polyketone polymerization catalyst of claim 1, wherein the acid of (C) is an inorganic acid having a pKa of 4 or less.

4. The polyketone polymerization catalyst of claim 3, wherein the acid of (C) is a perchloric acid, a sulfuric acid, a nitric acid, a phosphoric acid, a heteropoly acid, tetrafluorobroic acid, a hexafluorophosphoric acid, or a fluorosilicic acid.

5. The polyketone polymerization catalyst of claim 1, wherein the acid of (C) is a boron compound.

6. The polyketone polymerization catalyst of claim 5, wherein the acid of (C) is trispentafluorophenyl borane or trisphenylcarbeniumtetrakis (pentafluorophenyl) borate.

* * * * *